United States Patent [19]

Mesters et al.

[11] Patent Number: 4,725,573
[45] Date of Patent: Feb. 16, 1988

[54] COPPER-NICKEL CATALYST AND PROCESS FOR ITS PRODUCTION

[75] Inventors: Carolus M. A. M. Mesters, Utrecht; John W. Geus, Bilthoven; Eugène G. N. Kuijpers, Apeldoorn; Onno L. J. Gijzeman, Utrecht, all of Netherlands

[73] Assignee: VEG-Gasinstituut, N.V., Fed. Rep. of Germany

[21] Appl. No.: 32,974

[22] Filed: Apr. 2, 1987

Related U.S. Application Data

[63] Continuation of Ser. No. 684,456, Dec. 21, 1984, abandoned.

[30] Foreign Application Priority Data

Dec. 31, 1983 [DE] Fed. Rep. of Germany ....... 3347676

[51] Int. Cl.$^4$ .................... B01J 21/08; B01J 23/72; B01J 23/74
[52] U.S. Cl. .................... 502/245; 502/331; 518/713
[58] Field of Search ............. 1502/245, 331; 518/713

[56] References Cited

U.S. PATENT DOCUMENTS

| | | | |
|---|---|---|---|
| 2,234,246 | 3/1941 | Groombridge et al. | 518/713 |
| 3,371,050 | 2/1968 | Taylor et al. | 252/459 |
| 3,668,148 | 6/1972 | Van Beek et al. | 252/440 |
| 3,668,149 | 6/1972 | Geus et al. | 252/448 |
| 3,956,191 | 5/1976 | Cusumano | 252/474 |
| 3,962,140 | 6/1976 | Alcorn et al. | 502/315 |
| 4,113,658 | 9/1978 | Geus | 252/454 |
| 4,128,730 | 12/1978 | Reich | 502/245 X |
| 4,157,315 | 6/1979 | Michels et al. | 502/245 |
| 4,190,560 | 2/1980 | Geus et al. | 252/459 |

FOREIGN PATENT DOCUMENTS

| | | |
|---|---|---|
| 2025501 | 5/1971 | Fed. Rep. of Germany . |
| 1767202 | 5/1975 | Fed. Rep. of Germany . |
| 490090 | 8/1938 | United Kingdom . |
| 1220105 | 1/1971 | United Kingdom . |

OTHER PUBLICATIONS

Cratty et al., "Nickel, Copper and Some of Their Alloys as Catalysts for the Hydrogenation of Carbon Dioxide", J. Amer. Chem. Soc., vol. 80, pp. 767–773 (1958).

*Primary Examiner*—W. J. Shine
*Attorney, Agent, or Firm*—Schweitzer & Cornman

[57] ABSTRACT

A copper-nickel catalyst containing on an inert, refractory carrier metallic copper and nickel as active component bound to the carrier, characterized in that (a) the catalyst contains at least 5% by weight, based on the total weight of the catalyst, of metallic copper,
(b) the catalyst contains less than 20% by weight of metallic nickel, based on the total weight of metallic copper and metallic nickel, the catalyst containing at least 1% by weight of metallic nickel, based on the total weight of the catalyst,
(c) at least 80% by weight of the nickel is alloyed in the metallic copper,
(d) the copper-nickel-alloy is present on the carrier in small metal particles with an average particle size of less than 14 nm.

The invention also relates to the production of this catalyst and to its use for the reaction of carbon monoxide with hydrogen.

11 Claims, 1 Drawing Figure

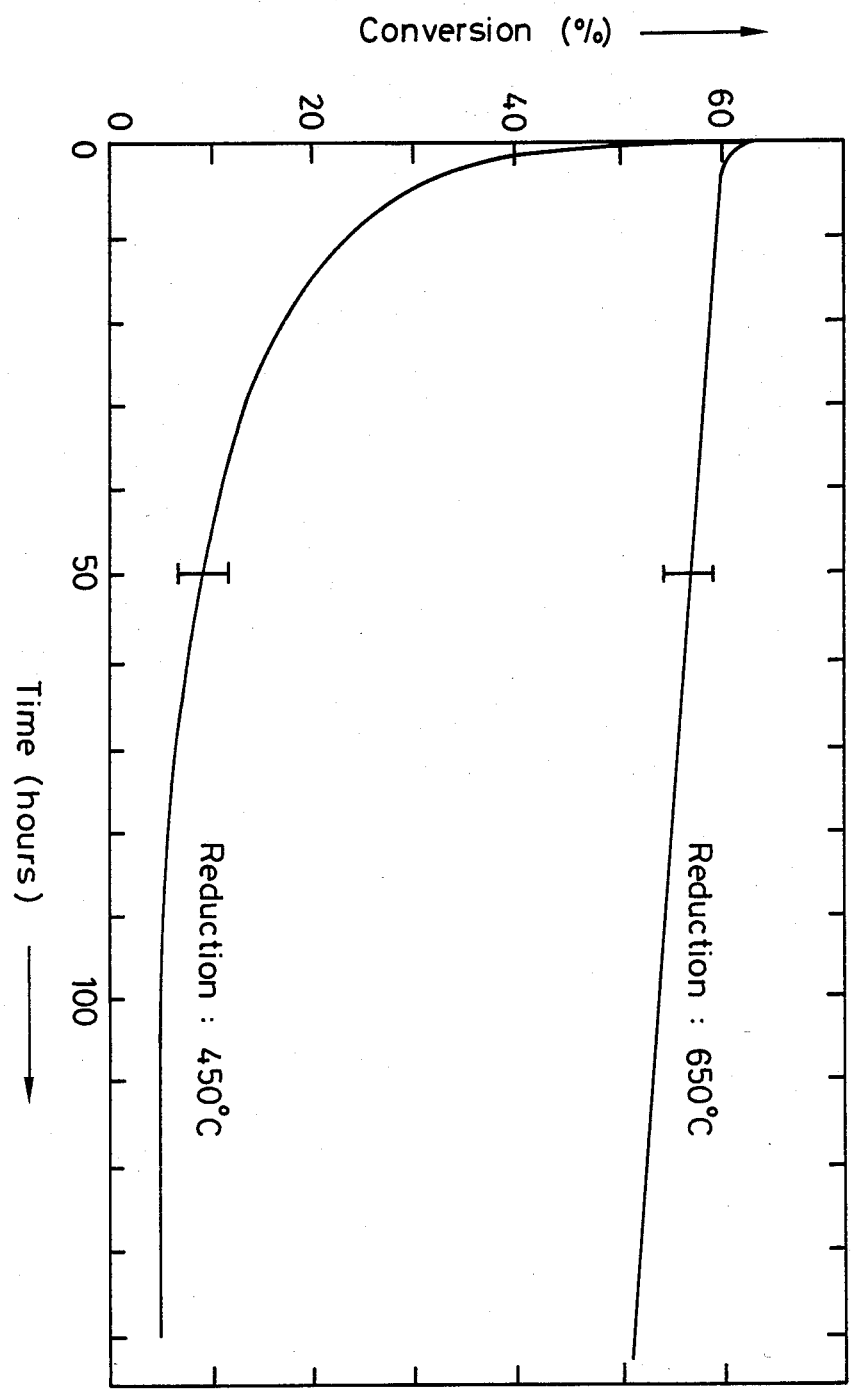

COPPER-NICKEL CATALYST AND PROCESS FOR ITS PRODUCTION

This is a file wrapper continuation application of application Ser. No. 684,456, filed Dec. 21, 1984, now abandoned.

BACKGROUND OF THE INVENTION:

This invention relates to a copper-nickel catalyst containing on an inert, refractory carrier metallic copper and nickel as active component bound to the carrier. The invention also relates to a process for producing that catalyst and to its use, in particular for the methanation reaction, in which carbon monoxide and hydrogen are reacted to form methane.

Copper-nickel catalysts containing metallic copper and nickel as the active component on an inert, refractory carrier are known, for example for DE-A-20 25 501, US- Pat. Nos. 4,157,315, 3,371, 050 and 3 956 191.

In the DE-A-20 25 501 copper-nickel catalysts are mentioned, where the nickel has a specific function in realizing thermostable copper catalysts. In this disclosure it is stated that thermostable copper catalysts cannot be produced by hitherto known methods, because of the weak interaction betweent the copper and the silica surface. Therefore, a method is proposed in which nickelhydrosilicate particles are formed onto the silica surface. An oxidic copper compound is then precipitated over the nickel compound particles. After reduction the copper particles are well-bounded to the carrier via the intermeidate layer of nickel-metal-nickel-silicate compounds. The nickel will thus not be active as nickel metal, because it is always covered by copper. Consequently these catalysts are only useful for their specific activity as copper catalysts, not as nickel or nickel-copper catalysts. Furthermore, because of the two-layer approach, it will be difficult to produce really small active metal particles. Average particles sizes of 17 and 200 Angstrom are mentioned (=17 and 20 nm respectively).

According to US. Pat. No. 4,157 315, a catalyst containing several metals, for example nickel and copper, as active component is produced by coating a substrate with a dispersion containing a stabilized solution of colloidal silicon dioxide and fine metal powders of the metals forming the active component, heating ths substrate thus coated in an inert gas atmosphere and sintering it at elevated temperature. A coating having low specific surface with low catalytic activity is obtained.

According to U.S. Pat. No. 3,371,050, nickel-copper catalysts can be produced by depositing insoluble compounds together onto the support from a solution of nickel salts and copper salts, separating off, calcining and reducing the loaded carrier. The catalysts thus obtained, in which the nickel content exceeds the copper content, have a small surface of active metals.

According to U.S. Pat. No. 3,956,191, nickel-copper catalysts are produced similarly to the disclosure of DE-A-20 25 501 by depositing an insoluble copper compound from a solution containing copper ions onto a carrier loaded with nickel and separating off, calcining and reducing the loaded carrier. Complete reduction of the nickel is not required and is extremely difficult. In addition, the catalysts described in this literature reference contain approximately twice as much nickel as copper.

The production of catalysts of the type in question is based on the general idea that, on the one hand, pure nickel catalysts tend to deposit carbon when exposed to an atmosphere containing CO or hydrocarbons, whereas on the other hand copper catalysts containing the active metals on an inert, refractory carrier are inactive for that reaction, but on the other hand do not show any tendency to deposit carbon. Accordingly, there is a need for copper-nickel catalysts which are suitable for the above-mentioned methanation reaction and other reactions, in which carbon monoxide and/or hydrocarbons are present in the reaction gas phase (as starting materials or end products) or are intermediately formed, and which catalyze those reactions, but which on the other hand do not show any tendency to deposit carbon.

The copper-nickel catalysts known from the prior art, which contain metallic copper and nickel as active component on an inert refractory carrier, show very poor catalytic activity for the above-mentioned reactions when the nickel content is low. On the other hand, if the nickel content is high, these catalysts present almost the same problems as pure nickel catalysts. The object of the present invention is to provide a copper-nickel catalyst which shows high catalytic activity for the methanation reaction and other reactions of the type described above, for example the low temperature reforming reaction, but which only deposits carbon after prolonged use, if at all. In addition, it would be of advantage if the catalysts in question did not show any tendency to form nickel carbonyls under operating conditions in chemical conversion processes.

It has now been found that this problem can be solved to a considerable degree by the catalyst defined hereinafter.

SUMMARY OF THE INVENTION

Accordingly, the present invention relates to a copper-nickel catalyst containing on an inert, refractory carrier metallic copper and nickel as active component bound to the carrier, characterised in that
(a) the catalyst contains at least 5% by weight, based on the total weight of the catalyst, of metallic copper,
(b) the catalyst contains less than 25 % by weight of metallic nickel, based on the total weight of metallic copper and metallic nickel, the catalyst containing at least 1 % by weight of metallic nickel, based on the total weight of the catalyst,
(c) at least 80 % by weight of the nickel is alloyed in the metallic copper,
(d) the copper-nickel alloy is present on the carrier in small metal particles with an average particle size of less than 14 nm.

BRIEF DESCRIPTION OF THE DRAWING

The FIGURE shows the conversion of the starting gas mixture of Example 2 to methane as a function of the period of operation of the reactor.

DETAILED DESCRIPTION OF THE INVENTION

The inert, refractory carrier used may be any of the materials having a large specific surface which are commonly used in the field of catalysts. Examples of those materials are aluminium oxide, silicon dioxide-aluminium oxide, silicon-dioxide-magnesium oxide, zirconium dioxide, silicon dioxide-zirconium dioxide, titanium dioxide, silicon dioxide-zirconium dioxide-titanium dioxide, crystalline or amorphous aluminosilicate molecular sieves and metal phosphates.

It is preferred to use a silicon dioxide carrier having a specific surface of more than 50 m²/g. It is possible to use the commercially available products based on kieselguhr, i.e. natural products, or synthetically produced, finely divided silicon dioxide, for example of the type commercially available as Aerosil(®). If kieselguhr is used, it should have a specific surface of from about 5 to 40 m²/g. However, in the production of the catalyst, the particles break up and a much larger surface of from about 60 to 150 m²/g is otained.

The upper limit to the quantity of metallic copper which is bound to the support depends essentially on the presence of a sufficient quantity of metallic copper and nickel having the above defined surface. In general, the upper limit amounts to approximately 50% by weight of metallic copper, based on the total weight of the catalyst.

It is preferred, that the weight ratio between copper and nickel in the catalyst is between 16 and 100. This means, that the catalyst contains on one part by nickel between 16 and 100 parts by weight copper. It is furthermore preferred, that the catalyst contains less than 13% by weight, more preferred less than 10% by weight of metallic nickel or even more preferred less than 6% by weight, based on the total weight of metallic copper and metallic nickel.

An essential feature of the catalyst according to the invention is that as large a percentage as possible of the nickel in the catalyst is present in the form of metallic nickel in the matrix of metallic copper. Preferably, at least 90% by weight and, more preferably, at least 95% by weight and most preferably 98% by weight of the nickel in the catalyst is alloyed in the metallic copper.

As pointed out above already it is an essential feature that the metal particles consisting of the copper-nickel-alloy have a very small particle size, and it is preferred that the average particle size of the metal particles is less than 12 nm, more preferably less than 10 nm and most preferably less than 8 nm.

Another preferred feature of the invention is, that the nickel alloyed in the metallic copper is distributed so homogeneously, that it is present in copper-nickel particles containing at most 30% by weight of metallic nickel, based on the total weight of metallic copper and metallic nickel.

The surface of the particles of metallic copper and nickel bound to the support best amounts to at least 20 and preferably to at least 40 m²/g of those metallic particles and best to at most 80 m²/g.

The present invention also relates to a process for producing the catalyst, characterized in that (a) copper compounds and nickel compounds are precipitated in a dilute solution, which contains the carrier suspended in finely divided form and copper ions and nickel ions in the desired ratio, by reaction with hydroxyl ions at a pH-value of from 3.5 to 6.5, accompanied by prolonged intensive stirring, and the loaded carrier is separated off from the solution, dried, calcined and reduced until at least 80% of the nickel in the catalyst has been reduced to metallic nickel, or (b) nickel carbonyl is allowed to act on a catalyst which contains metallic copper in finely divided form on an inert, refractory carrier and of which the temperature is above 100° C.

It is preferred to allow the nickel carbonyl to act on the coppercontaining catalyst used as starting material in a fluidised bed reactor in which the catalyst particles are present in fluidised form.

In method a) the catalyst is preferably reduced until at least 90% by weight and, more preferably, at least 95% by weight of the nickel in the catalyst has been reduced to metallic nickel. The reduction step is carried out at temperatures at which that degree of reduction is achieved. The temperatures in question are preferably temperatures in the ranges from about 500 to 800° C. maintained for relatively long periods, for example of from about 20 to 100 hours.

In another embodiment, it is preferred thoroughly to mix the catalyst containing metallic copper with nickel powder and to allow carbon monoxide to act on the resulting mixture, so that nickel carbonyl is formed in situ.

During production, the temperature of the catalyst containing metallic copper is best below 700° C. It is also of advantage for the nickel carbonyl to be present in admixture with non-oxidizing gases, preferably nitrogen, the content of nickel carbonyl in the gas mixture amounting to at least 0.1% by volume, preferably to between 0.5 and 1.5% by volume and, more preferably, to between 0.6 and 1.1% by volume. The catalyst containing metallic copper used as starting material best contains from 5 to 50% by weight of copper, based on the total weight of the support plus metallic copper.

Where production is carried out in a fluidised bed reactor, the catalyst particles best differ as little as possible from one another in particle size so that a satisfactory fluidised bed is obtained and particularly large, heavy particles do not sink to the bottom or particularly light, small particles float to the top. Accordingly, the particle size of the catalyst particles best shows a narrow deviation range, preferable of ±20% from that particle size which is common to most of the particles. This is known to the expert on the subject of fluidised bed reactions. The average particle size is best in the range from about 0.05 to 1.0 mm.

It is of course important to ensure that the nickel carbonyl does not decompose outside the fluidised bed. Accordingly, the entrance to the reactor should be cooled, best to temperatures below about 150° C. and preferably to temperatures below about 100° C. The same also applies to the screen by which the fluidised bed is closed off underneath. In order to heat the catalyst particles above the screen in the fluidised bed as quickly as possible to the desired temperature, hot inert gases for heating the catalyst particles are best introduced in a zone above the cooled sieve by which the fluidised bed is closed off underneath. In the case of small reactors, the desired temperature gradient may be obtained by external heating and cooling systems.

In the process variant in which the nickel powder is exposed to the effect of carbon monoxide in admixture with the copper catalyst used as starting material, it can be of advantage alternately to heat the mixture to relatively high and then to cool to somewhat lower temperatures, for example initially to keep it at a relatively low temperature of from about 100° C. to 250° C. for a certain period, for example from 10 minutes to 2 hours, and then at a higher temperature, best at least 100° C. higher, for a certain period, for example from 10 minutes to 2 hours, and then to cool it again, best by at least 100° C., and to repeat this heating/cooling cycle either once or several times. The nickel particles react with the carbon monoxide at relatively low temperatures until an equilibrium state in regard to the formation of nickel carbonyl has been established in the reactor. At elevated temperature, nickel carbonyl is less stable, i.e. decomposes, preferably at the copper surface. In this way, metallic nickel is transported into the metallic copper which forms the matrix. If the cooling/heating cycle is then applied again, that mechanism is repeated until the required nickel content has been reached in the copper or until all the powder-form nickel added has been transported into the copper.

Despite its relatively low nickel content, the catalyst according to the invention shows high activity, for example in the methanation reaction, whereas on the other hand the deposition of carbon is almost completely avoided. This must be attributed to the particular structure of the catalyst as defined above. The particles of metallic copper and nickel are present in the form of very small particles, as is evident from the large surface as defined in the foregoing.

On the basis of certain studies, the inventors gained the impression that, in a gas atmosphere containing carbon monoxide, the nickel migrates to the surface of the copper particles in which the nickel is distributed and that, in this way, the nickel is able to exert its catalytic activity on the methanation reaction, the low-temperature reforming reaction and other reactions. The fact that the nickel is present in the copper matrix prevents the formation of nickel carbonyls. The formation of nickel carbonyl can lead to the formation of relatively large nickel particles on which carbon can be formed or deposited. To prevent this, the nickel must be present in metallic form in the metallic copper particles in the quantity defined above, whereas on the other hand the nickel content must remain within the range defined above. If the nickel content exceeds the upper limit defined in accordance with the invention, the concentration of nickel at the surface of the copper matrix would also appear to increase to such an extent that nickel carbonyls are more easily formed. If, on the other hand, the nickel is not present in metallic form in the copper matrix, but instead is bound in ionic form to the support material, it is impossible for nickel to migrate to the surface of the copper matrix to an adequate extent when the catalyst is used for the above-mentioned reactions and the activity of the catalyst is then too low to be able to carry out the reactions satisfactorily on an industrial scale.

Accordingly, an essential feature of the catalyst according to the invention is that the nickel is present in metallic form in the copper particles in such a way that, in the presence of carbon monoxide in the gas atmosphere, the nickel particles migrate to the copper surface where they exert their catalytic activity on the above reactions. On the other hand, the quantity of nickel at the copper surface should not be so large as to result in carbonyl formation. These facts as discovered by the inventors are surprising to the expert because, hitherto, it had generally been assumed that useful nickel-copper catalysts should have a relatively high nickel content and because no attention was paid to the fact that the nickel must be present in metallic form in the copper matrix.

The metallic state is generally obtained by the reduction of metal compounds deposited on the carrier with hydrogen. In one variant of the process, therefore, the last stage in the production of the catalyst is the reduction step. On account of the poor accessibility of some nickel particles, the reduction step cannot always be carried out completely to metallic reduced nickel. According to the invention, it is not harmful for the catalyst to contain a small quantity of nickel compounds which have not been reduced of metallic nickel. The important requirement is that metallic nickel should be present in the copper-particles in the quantity defined above.

The catalyst according to the invention may be produced by various methods. In the main, two processes are suitable for its production, namely: the so-called carbonyl method, which is described in detail in the U.S. Patent Application filed at the same time (official Ser. No. 684,621) under the title "A Process for the Production of a Catalyst", and secondly production by precipitating basic copper and nickel compounds from a solution containing copper and nickel ions onto the carrier suspended therein, separating off the loaded carrier from the solution, calcining and reducing the loaded carrier. The carbonyl method has amongst other the advantage that the reduction step to produce an active catalyst can largely be avoided.

The catalyst according to the invention may be used with advantage, for example for the following reactions:

Methanation, i.e. the reaction of carbon monoxide with hydrogen to form methane and steam.

The low-temperature reforming reaction, in which hydrocarbons are reacted with steam to form methane and carbon dioxide at temperatures in the range about 350° to 500° C.

The shift reaction, i.e. the reaction of carbon monoxide with steam to form hydrogen and carbon dioxide. However, the catalyst according to the invention is not particularly selective in that reaction at temperatures above 450° C.

The shift-methanation reaction, in which carbon monoxide is reacted with hydrogen and/or steam in various quantitative ratios to form methane and carbon dioxide.

Selective hydrogenation reactions of various kinds.

One feature common to all these reactions is that carbon monoxide and/or hydrocarbons are present in the gas phase on the catalyst as starting materials or as reaction products, possibly even on an intermediate basis. These reactions are carried out in known manner using the catalyst according to the invention.

Particularly high activity with very little danger of carbon deposits was observed in the case of the above-mentioned methanation reaction. In this case, the entry temperature for the methanation reactor can be kept very low, for example in the range from about 250 to 350° C. Since considerable quantities of nickel carbonyl are formed in state-of-the art processes, the exit temperatures of the methanation reactor have to be kept so high that the nickel carbonyl is redissociated at the temperatures in question and, hence, is unable to pass into the waste gas stream, which must be strictly avoided (inter alia on account of the high toxicity level). According to the invention the exit temperatures can be kept lower, for example below about 550° C. and preferably below 500° C.

The presence of monometallic nickel particles in the catalyst can be detected by magnetic methods. It is known that, at temperatures above 60° K., copper-nickel alloys containing less than 30 atom % of nickel are diamagnetic (cf. H.C. van Elst et al, Physica 20 (1962) 1297). As a result, if all the nickel present is alloyed with copper, only very weak magnetization, which is not dependent on temperature, is measured, even in a strong magnetic field of, for example, $10^4$Oe. If, however, a significant quantity of the nickel in the catalyst is present in the form of monometallic crystallites, these particles show superparamagnetism (cf. Selwood in "Chemisorption and Magnetization") or even ferromagnetism. The presence of ferromagnetic particles produces a steep increase in magnetization for a given strength of the magneti field. The magnetization of superparamagnetic particles is temperature-dependent. Nickel-copper alloys with a nickel content of from 30 to 50 atom % show weak paramagnetism which, compared with monometallic nickel particles, gives rise to only weak magnetization. 30 atom % of nickel in the nickel-copper alloy corresponds to about 28 % by weight of nickel. The paramagnetic moment of the reduced catalyst is no higher than 1.0 $\mu m_b$ per nickel atom and/or nickel ion.

The infrared absorption spectra of CO irreversibly adsorbed on Cu-Ni-alloy catalysts show only one wide adsorption band at around 2000 $cm^{\mu}1$. It is known that CO adsorbed on pure copper catalysts is readily desorbed, whereas CO adsorbed on pure nickel catalysts cannot be desorbed by evacuation at room temperature. Accordingly, the adsorption band observed after evacuation must be attributed to CO adxorbed at "Ni-like" places.

On pure Ni-catalysts, irreversibly adsorbed CO gives rise to two adsorption bands, the band with a maximum at 2045 $cm^{-1}$ being attributed to linearly bound CO and the other band with a maximum at 1950 $cm^{-1}$ being attributed to bridge-bound CO. J. A. Dalmon, M. Primet, G. A. Martin and B. Imelik, Surface Sci., 50 (1975) 95 observed that the maxima of both bands were shifted to lower frequencies when a nickel-on-silica gel catalyst was alloyed with copper. In addition to the frequency shift, they also observed a reduction in the absorption intensity of both bands with increasing copper content. The bands assigned to bridge-bound CO showed a very much greater reduction than the band assigned to linearly bound CO. This was explained by the fact that a larger number of nickel atoms per binding place is required for bridge-bound CO than for linearly bound CO. In fact, the absorption band of bridge-bound CO disappears completely at copper contents above 50 %.

The frequency shift is necessarily indicative of the fact that, after exposure to a CO-atmosphere, our completely reduced copper-nickel catalysts show a surface composition in which nickel is present as an isolated dilute species in a copper matrix.

When the copper-nickel catalysts are produced by the carbonyl process, in which a copper-silicon catalyst is thoroughly mixed with finely divided powder, which is not present in monocrystalline form and, accordingly, shows crystal boundaries between the individual crystallites, it is important that all such nickel should be consumed during production of the catalyst and should not remain behind in the catalyst as nickel powder, because otherwise it would give rise to the formation of carbon deposits. If, however, nickel powder which is present solely in monocrystalline form and does not show any partice boundaries, is used in the production of the catalyst, it is not absolutely necessary for all the nickel powder to be consumed by reaction with carbon monoxide.

If the catalyst according to the invention is used for catalytic reactions at temperatures below about 400° C. or, in some cases, below about 500° C., it must be treated before use, i.e. after the reduction step, if any, in a gas atmosphere containing carbon monoxide, the carbon monoxide partial pressure best amounting to between about 0.05 and 4 MPa and the temperature of the catalyst to between about 400° and 600° C. and preferably to between about 400 and 500° C. The treatment is best carried out for at least 15 minutes, a period of 60 minutes generally being sufficient as the upper limit. The catalyst is specially activated in this way. In practice, this special activation may also be carried out in situ providing carbon monoxide, preferably under the partial pressures mentioned above, and the temperatures mentioned above are present during the use of the catalyst in the gas phase. The terms "carrier" and "support" are equivalent.

PRODUCTION EXAMPLE 1

The starting material is a copper-silicon dioxide catalyst which is produced in known manner by homogeneously forming hydroxyl ions through the decomposition of dissolved urea at around 90° C. in a suspension of the finely divided silicon dioxide of large specific surface, which is used as the carrier, in an aqueous solution of a copper salt and thus depositing copper in the form of oxidic compounds on the carrier (cf. DE-PS 1 767 202). The silicon dioxide used is a commercially available product (Aerosil ®) having a surface of 200 $m^2$/g. The loaded carrier, which contains approximately 30% by weight of metallic copper, based on the total weight of the charged carrier, was dried for 20 hours at 110° C., ground and sieved. The fractions with particle sizes of from 0.2 to 0.7 mm ±0.05 mm were used for further processing. The subsequent reaction was carried out in a fluidised bed reactor.

The catalyst which is present in fluidsed form was calcined by passing over a mixture of 10 % by volume of oxygen and 90 % by volume of nitrogen at 400° C. The catalyst was then reduced by passing a mixture of 10 % by volume of hydrogen and 90 % by volume of nitrogen through the fluidised bed reactor for 5 hours at 430° C. The nitrogen is used to ensure that a sufficiently vigorous gas stream keeps the catalyst in the fluidised state.

In a small stainless steel reactor (holding capacity 50 cc), nickel carbonyl was produced by treating nickel pellets, which had been reduced for 48 hours at 450° C. in an atmosphere of equal parts by volume of hydrogen and argon, with carbon monoxide at a temperature of 70° C. and under a pressure of 0.3 MPa.

The resulting mixture of nickel carbonyl and carbon monoxide was introduced into a gas mixing chamber in a quantity of 50 ml/minute together with a gas stream of hydrogen (5%), argon (5%) and nitrogen (90%) in a quantity of about 4 liters/minute. The hydrogen was used to prevent oxidation of the reduced metal particles by any oxygen impurities possibly present in the large quantity of nitrogen used. The gas stream leaving the gas mixing chamber was introduced into the fluidised bed reactor containing the copper catalyst in fluidised form. The temperature of the catalyst in the fluidised bed reactor during decomposition of the nickel carbonyl amounted to between 300 and 35° C. At that temperature, the nickel carbonyl dissociates completely on copper monocrystals. To prevent the nickel carbonyl Ni(CO)$_4$ from decomposing before reaching the catalyst under the effect of excessive temperatures below or inside the (glass) filter which forms the lower boundary of the fluidised bed, only the upper part of the reactor above the (glass) filter was heated. The lower part was cooled by an air stream. As a result, the nickel was only deposited above the filter, visible deposition of nickel occurring in the lower part. Samples of the catalyst were removed from the reactor at various time intervals and analysed. The nickel content was determined by atomic absorption spectroscopy (AAS). Analysis was carried out by dissolving a certain quantity of the catalyst in a mixture of nitric acid and hydrochloric acid in which the active metals dissolve completely in contrast to the silicon dioxide. The silicon dioxide particles were centrifuged off from the solution and washed because these solid particles would interfere with the AAS-measuremente. The quantity of nickel in the acid solution was measured at a wavelength of 352.4 nm in an acetylene air flame. The large quantities of copper presented no problems in that respect. The characteristic data of a bimetallic catalyst obtained in this wax are shown in the following Table:

| | |
|---|---|
| Copper content (completely reduced catalyst) | 29.1% by weight |
| Nickel content | 4.0% by weight |
| BET-surface | 450 m$^2$/g |
| Specific metal surface | |
| per gram of catalyst | 19 m$^2$ |
| per gram of metallic copper and nickel | 64 m$^2$ |
| Mean particle size | 11 nm |

(The values indicated above are averages of values determined by various methods, namely: electron microscopy, X-ray line widening and the degree of chemisorption.)

Less than 1% by weight of the total weight of the nickel is not alloyed in copper particles.

PRODUCTION EXAMPLE 2

1000 ml of a solution of 12.2 g of urea per liter of water were introduced into a 2.5 liter vessel. 10 g of finely divided silicon dioxide (Aerosil ®) were then suspended in that solution and the pH-value adjusted with nitric acid to pH 2. After heating to 90° C., the pH-value increased through decomposition of the urea, hydroxyl ions being homogeneously released. Then the pH-value reached pH 5.8, the injection of a copper-nickel solution at a rate of 0.4 cc per minute was commenced. The copper-nickel solution had been prepared by dissolving 16.3 g of Cu(NO$_3$)$_2$.3H$_2$O and 1 g of Ni(NO$_3$)$_2$.6H$_2$O in 500 cc of water and adjusting the pH-value to pH 2 by the addition of nitric acid. The pH-value was automatically kept at pH 5.8 by a pH-stat through the injection of nitric acid.

In some cases, the pH-value was not kept at a constant level by the injection of acid. In those cases, the initial rate of injection of the copper-nickel nitrate solution was greater and the pH-value rose constantly to a value of pH 6.3, after which injection was terminated.

Precipitation may also be carried out by using potassium cyanate instead of urea as the agent for homogeneously forming hydroxyl ions. In that case, however, precipitation is carried out at 40° C. instead of 90° C. After the copper-nickel nitrate solution had been introduced, the deposit was separated off from the solution, washed and dried for 20 hours at 110° C.

The catalyst was reduced for 70 hours at 650° C. in a gas atmosphere containing 10 % by volume of hydrogen, remainder nitrogen, the catalyst being obtained in its active form.

PRODUCTION EXAMPLE 3

20 g of a catalyst containing 30 % by weight of metallic copper, based on the total weight of the catalyst, on finely divided silicon dioxide/Aerosil ® as carrier was throughly mixed with 1 g of a very fine nickel powder (particle size 0.7 μm) and the resulting mixture tabletted. The nickel powder had been obtained from nickel carbonyl and was essentially present in the form of monocrystalline nickel crystals. This mixture of catalyst and nickel powder was reduced for 6 hours at 430° C. in a gas stream containing 10 % by volume of hydrogen and 90 % by volume of nitrogen. The mixture was then cooled to 100° C. and subsequently exposed for about 1 hour to a CO-atmosphere under a pressure of approximately 0.1 MPa. After this treatment, the temperature in the reactor was increased to 450° C. at a rate of 6° C. per minute and then kept at that level for 15 minutes. The mixture was then cooled to 110° C. This process of increasing and lowering the temperature was repeated twice. After the third temperature increase, a sample was removed from the reactor and analysed avoiding oxidation of the catalyst.

As much of the nickel powder as possible was magnetically removed. The remaining catalyst was examined by infrared spectroscopy of absorbed carbon monoxide. The presence of pure nickel is indicated by the band at 2045 cm$^{-1}$. However, a band was also observed at 2005 cm$^{-1}$, indicating that about 5% by weight of nickel, based on the total weight of nickel and copper, were present in the catalyst an an alloy with copper. (Measuring techniques are described in Surface Science 50 (1975) 95-108).

EXAMPLE 1

Carrying out the methanation reaction by reacting CO with H$_2$

A gas mixture containing 50% by volume of H$_2$ and 50% by volume of CO is passed over the catalyst under a total pressure of 0.1 MPa, at a temperature of 400° C. and at a space velocity of 300 per hour. A catalyst obtained in accordance with Production Example 1 was used, containing 1.5% by weight of metallic nickel, based on the total weight of the catalyst. The copper content amounts to 30% by weight, based on the total weight of the catalyst. The content of metallic nickel, based on the total weight of metallic nickel and metallic copper, amounts to approximately 4.7% by weight. The relative conversion to methane obtained is 60%. This conversion level decreases only slightly, even after the reaction has been carried out for more than 100 hours.

EXAMPLE 2

Catalyst obtained in accordance with Production Example 2 (nickel content 10% by weight, based on the copper content) is used for the methanation reaction, the starting mixture having the following composition: 10% of H$_2$, 10% of CO, 80% of N$_2$. Space velocity 1500 per hour. FIG. 1 shows the conversion of the starting gas mixture to methane as a function of the period of operation of the reactor. It can be seen from FIG. 1 that, even after prolonged operation of the reactor, there is only a slight reduction in the conversion level. This is attributable to the composition of the catalyst corresponding to the definition of the present invention.

If reduction of the catalyst is inadequate and unless at least 80% of the nickel bound to the carrier are uniformly distributed as metallic nickel in the metallic copper, a reduction in the conversion level occurs considerably earlier.

We claim:

1. A copper-nickel catalyst containing on an inert, refractory carrier metallic copper and nickel as active component bound to the carrier, characterised in that
   (a) the catalyst contains at least 5% by weight, based on the total weight of the catalyst, of metallic copper,
   (b) the catalyst contains less than 25% by weight of metallic nickel, based on the total weight of metallic copper and metallic nickel, the catalyst containing at least 1% by weight of metallic nickel, based on the total weight of the catalyst,
   (c) at least 80% by weight of the nickel is alloyed in the metallic copper,
   (d) the copper-nickel-alloy is present on the carrier in small metal particles with an average particle size of less than 14 nm.

2. A catalyst as claimed in claim 1, characterised in that weight ratio between copper and nickel in the catalyst is between 16:1 and 100:1.

3. A catalyst as claimed in claim 1, characterised in that the average particle size of the metal particles is less than 12 nm.

4. A catalyst as claimed in claim 1, characterised in that the average particle size of the metal particles is less than 10 nm.

5. A catalyst as claimed in claim 1, characterised in that the average particle size of the metal particles is less than 8 nm.

6. A catalyst as claimed in claim 1 characterised in that at least 90% by weight of the nickel in the catalyst is alloyed in the metallic copper.

7. A catalyst as claimed in claim 1 characterised in that at least 95% by weight of the nickel in the catalyst is alloyed in the metallic copper.

8. A catalyst as claimed in claim 1 characterised in that the nickel alloyed in the metallic copper is distributed so homogenously, that it is present in copper-nickel particles containing at most 30% by weight of metallic nickel, based on the total weight of metallic copper and metallic nickel.

9. A catalyst as claimed in claim 1 characterised in that the carrier is finely divided silicon dioxide having a specific surface of more than 50 $m^2/g$.

10. A catalyst as claimed in claim 1 characterised in that it contains less than 6% by weight of metallic nickel, based on the total weight of metallic copper and metallic nickel.

11. A process for producing the copper-nickel catalyst claimed in claim 1, characterized in that
   (a) copper compounds and nickel compounds are precipitated in a dilute solution, which contains the carrier suspended in finely divided form and copper ions and nickel ions in desired ratio, by reaction with hydroxyl ions at a pH-value of from 3.5 to 6.5, accompanied by prolonged intensive stirring, and the loaded carrier is separated off from the solution, dried, calcined and reduced until at least 80% of the nickel in the catalyst has been reduced to metallic nickel.

* * * * *